(12) United States Patent
Gallagher et al.

(10) Patent No.: US 7,001,412 B2
(45) Date of Patent: Feb. 21, 2006

(54) SURGICAL CLIP WITH INTEGRAL SUTURE-SECURING MECHANISM

(75) Inventors: Richard J. Gallagher, Raleigh, NC (US); Lowell M. LaFreniere, Raleigh, NC (US)

(73) Assignee: Pilling Weck Incorporated, Research Triangle, NC (US)

( * ) Notice: Subject to any disclaimer, the term of this patent is extended or adjusted under 35 U.S.C. 154(b) by 163 days.

(21) Appl. No.: 10/766,800

(22) Filed: Jan. 28, 2004

(65) Prior Publication Data

US 2005/0165424 A1    Jul. 28, 2005

(51) Int. Cl.
*A61B 17/04* (2006.01)

(52) U.S. Cl. ............... 606/232; 606/151; 606/157; 606/158; 606/233

(58) Field of Classification Search ........... 606/120, 606/139, 142, 148, 151, 157, 158, 215, 221, 606/232, 233
See application file for complete search history.

(56) References Cited

U.S. PATENT DOCUMENTS

| | | | |
|---|---|---|---|
| 4,487,205 A | * | 12/1984 | Di Giovanni et al. ...... 606/158 |
| 4,498,476 A | * | 2/1985 | Cerwin et al. ............. 606/158 |
| 5,078,731 A | | 1/1992 | Hayhurst |
| 5,100,416 A | | 3/1992 | Oh et al. |
| 5,282,832 A | | 2/1994 | Toso et al. |
| 5,330,442 A | | 7/1994 | Green et al. |
| 5,376,101 A | | 12/1994 | Green et al. |
| 5,474,572 A | | 12/1995 | Hayhurst |
| 5,514,159 A | | 5/1996 | Matula et al. |
| 5,649,937 A | * | 7/1997 | Bito et al. ................. 606/139 |
| 5,658,300 A | * | 8/1997 | Bito et al. ................. 606/143 |
| 5,797,931 A | * | 8/1998 | Bito et al. ................. 606/151 |
| 5,906,625 A | * | 5/1999 | Bito et al. ................. 606/142 |
| 6,440,154 B1 | * | 8/2002 | Gellman et al. ........... 606/232 |

* cited by examiner

*Primary Examiner*—Glenn K. Dawson
*Assistant Examiner*—Michael Mendoza
(74) *Attorney, Agent, or Firm*—Baker & Hostetler LLP

(57) ABSTRACT

A polymeric, surgical clip having first and second curved leg members joined at their proximal end by a hinge portion and movable from an open position to a closed position for securing and maintaining a desired amount of tension on a suture. A ridge protrudes from a portion of the inner surface of one leg and a groove is formed in a corresponding portion of the inner surface of the other leg. An eyelet extends through the ridge to engage a portion of a suture.

17 Claims, 5 Drawing Sheets

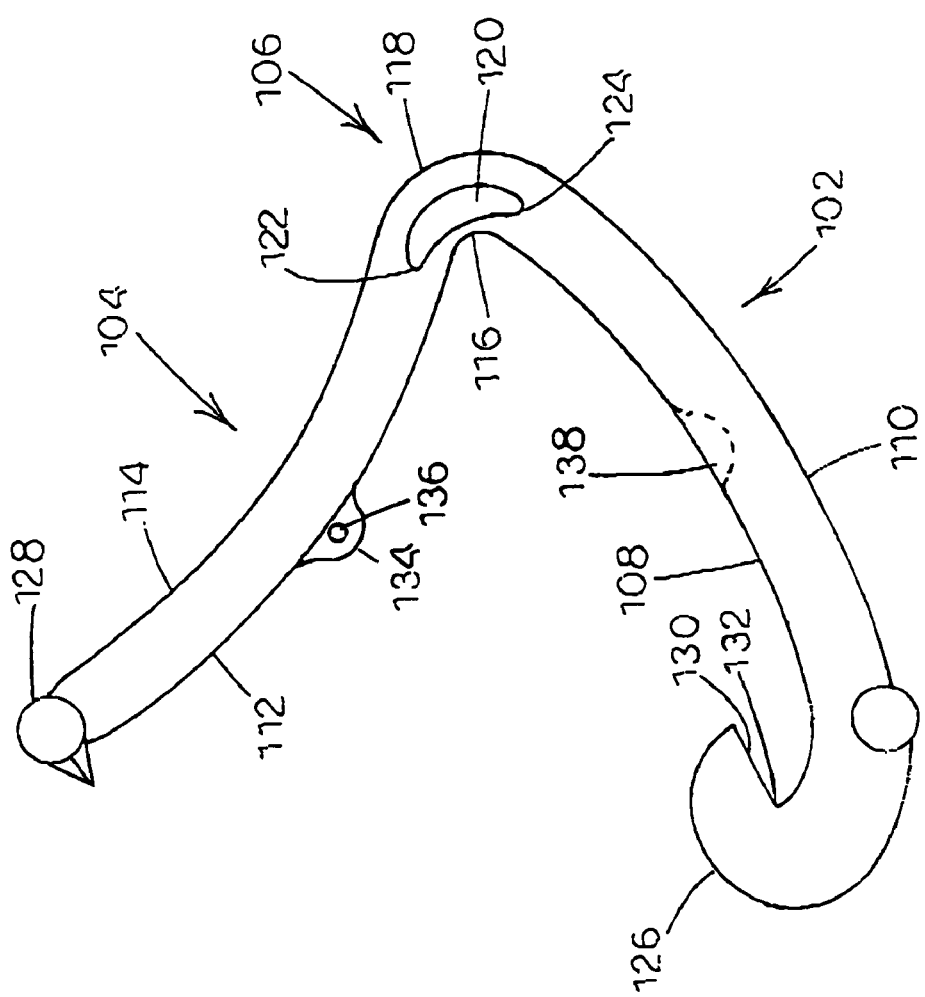
Fig. 2-A

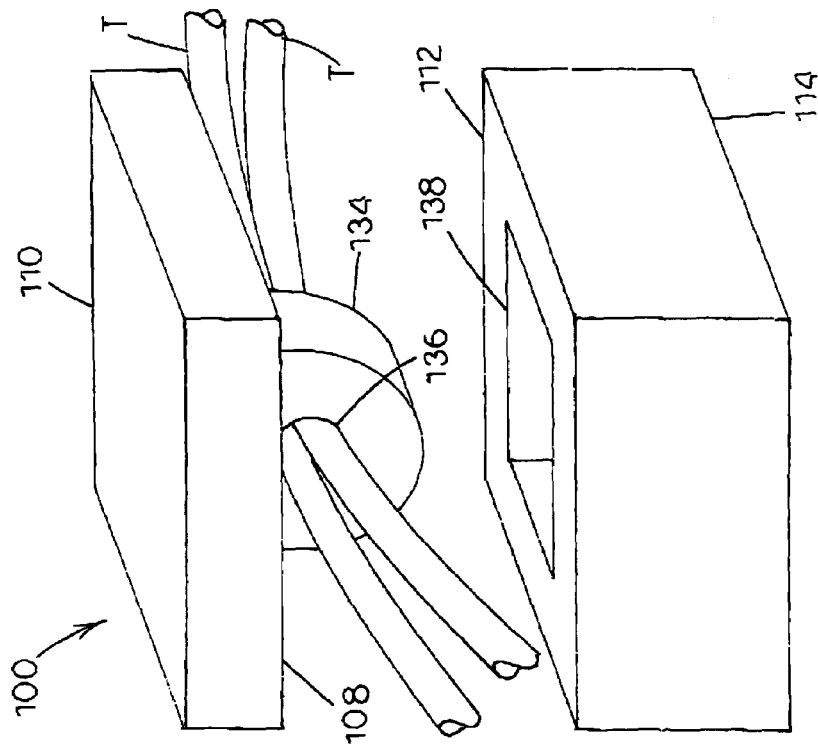
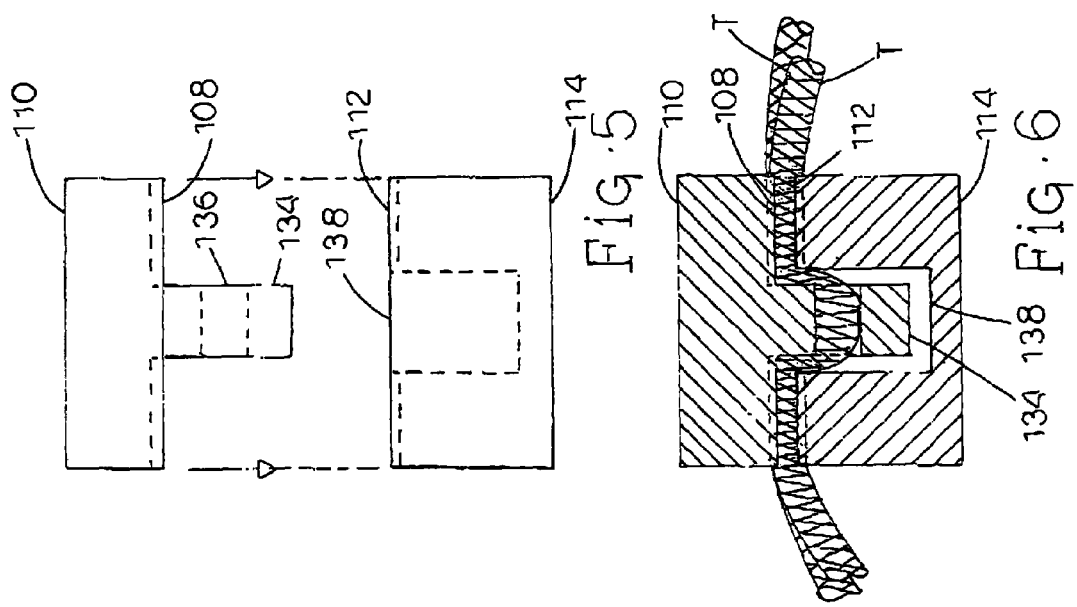

SURGICAL CLIP WITH INTEGRAL SUTURE-SECURING MECHANISM

TECHNICAL FIELD

The present invention relates to surgical clips, and more particularly to surgical clips with an integral suture-securing mechanism to engage the ends of a suture to maintain a desired amount of tension on the suture. Yet more particularly, the present invention relates to an improved surgical clip that is provided with a suture-securing mechanism integral to the legs of the clip that serve to secure the ends of a suture.

BACKGROUND ART

Laparoscopic, endoscopic, and other minimally invasive surgical techniques enable surgeons to perform fairly complicated procedures through relatively small entry points in the body. The term "laparoscopic" refers to surgical procedures performed on the interior of the abdomen, while the term "endoscopic" refers more generally to procedures performed in any portion of the body. Endoscopic surgery involves the use of an endoscope, which is an instrument permitting the visual inspection and magnification of a body cavity. The endoscope is inserted into a body cavity through a cannula extending through a hole in the soft tissue protecting the body cavity. The hole is made with a trocar, which includes a cutting instrument slidably and removably disposed within a trocar cannula. After forming the hole, the cutting instrument can be withdrawn from the trocar cannula. A surgeon can then perform diagnostic and/or therapeutic procedures at the surgical site with the aid of specialized medical instruments adapted to fit through the trocar cannula.

Some known advantages of minimally invasive surgical techniques include reduced trauma to the patient, reduced likelihood of infection at the surgical site, and lower overall medical costs. Accordingly, minimally invasive surgical techniques are being applied to an increasingly wider array of medical procedures.

Surgical procedures often involve using sutures to hold tissue together while the tissue heals. Tension is applied to the suture to pull the tissue together and the suture is secured by tying the free ends of the suture to form a knot. The knotted ends prevent the suture from prematurely coming free from the suture site. However, once the ends of a suture are knotted, it has proven difficult to adjust the tension of the suture without removing the knot, such as by cutting the suture. Moreover, suturing internal tissue during minimally invasive procedures can prove challenging due to the limited amount of space available to perform the rather complex manipulations required to knot the suture.

Accordingly, there is a need to provide a mechanism to secure the free ends of a suture while maintaining a desired amount of tension on the suture.

SUMMARY OF THE INVENTION

In accordance with the present invention, a polymeric surgical clip having a first and second leg member is provided. Each leg member has an inner surface and an opposite outer surface. A resilient hinge joins the first leg member and the second leg member at their proximal ends, with the first and second leg members being oriented such that the inner surface of the first leg member is in opposition to the inner surface of the second leg member. A deflectable hook member terminates the distal end of the first leg member and is curved toward the second leg member. A locking portion terminates the distal end of the second leg member and is complementary to the hook member such that when the first and second leg members are moved about the hinge from an open position to a closed position, the hook member deflects about the distal end of the second leg member to lock the clip in the closed position. A ridge is formed along the inner surface of either the first or second leg members and a groove is formed along the inner surface of the other leg. The groove is aligned in opposition to the ridge such that the ridge and groove cooperate when the clip is in the closed position to capture a portion of a suture and maintain a desired level of tension on the suture. The ridge includes an eyelet that extends through the ridge and engages a portion of the suture.

The surgical clip of the present invention is preferably made of polymeric material and accordingly minimizes interference with high technology diagnostic modalities such as CAT SCAN, MRI and MRS. At the same time, the clip is nearly as small as comparable metal clips while maintaining sufficient strength and possessing high security in the clip's latching mechanism in the closed position clamping the vessel. The surgical clip is configured to provide a secure means of handling an application to avoid premature release from the applier of the clip.

It is an object of the present invention to provide a mechanism for securing the ends of a suture while maintaining a desired amount of tension on the suture.

Some of the objects of the invention having been stated hereinabove, other objects will become evident as the description proceeds when taken in connection with the accompanying drawings as best described hereinbelow.

BRIEF DESCRIPTION OF THE DRAWINGS

FIG. 2-A is an enlarged side elevation view of the surgical clip according to another embodiment of the present invention;

FIG. 4 is an enlarged, fragmentary perspective view of the ridge and groove portions of the surgical clip according to one embodiment of the present invention;

FIG. 5 is a vertical cross-sectional view of the ridge and groove portions of the surgical clip according to one embodiment of the present invention;

FIG. 6 is a vertical cross-sectional view of the clip applied to a suture;

DETAILED DESCRIPTION OF THE INVENTION

Figure 1:
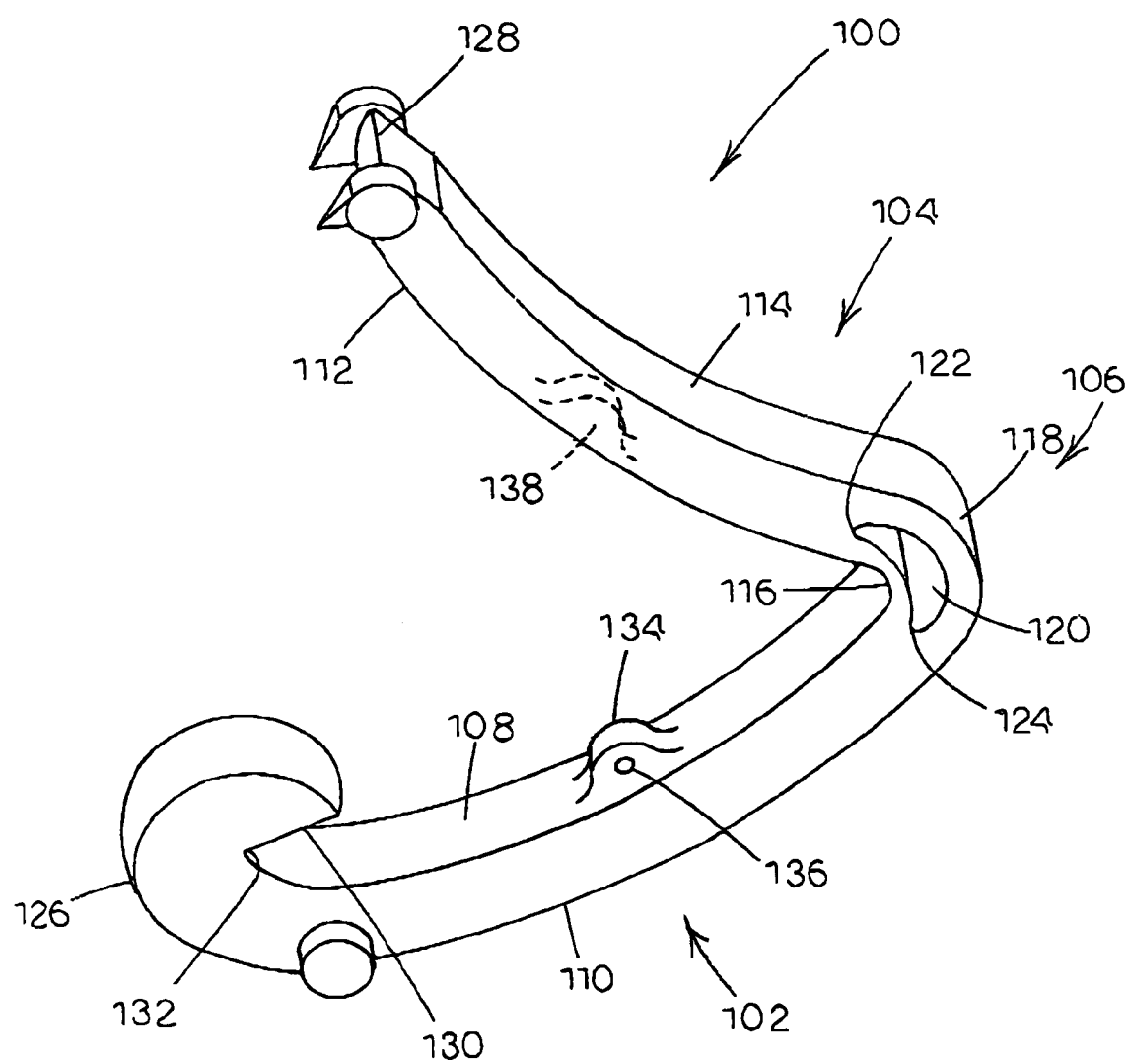
FIG. 1 is an enlarged perspective view of a surgical clip according to one embodiment of the present invention.
Figure 3:
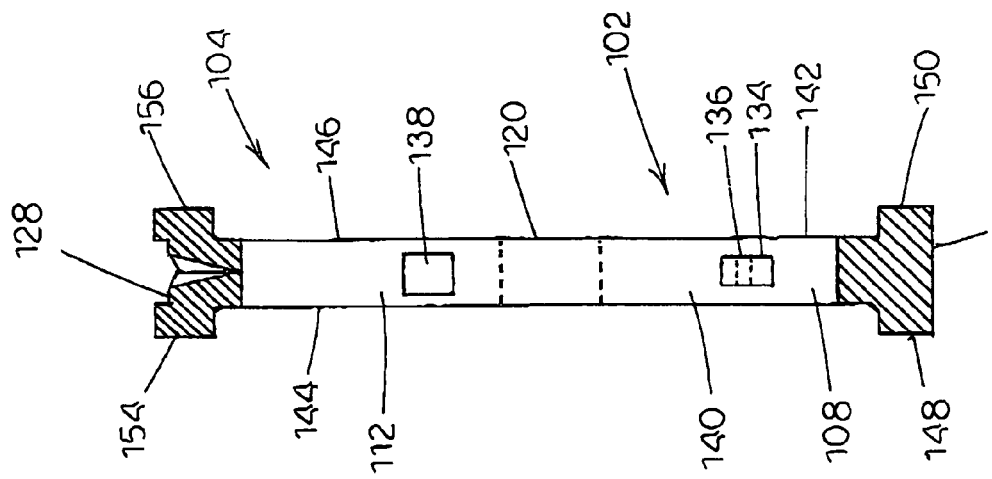
FIG. 3 is an enlarged, partially sectioned view of the surgical clip viewed along line 3—3 in FIG. 2.
Figure 2:
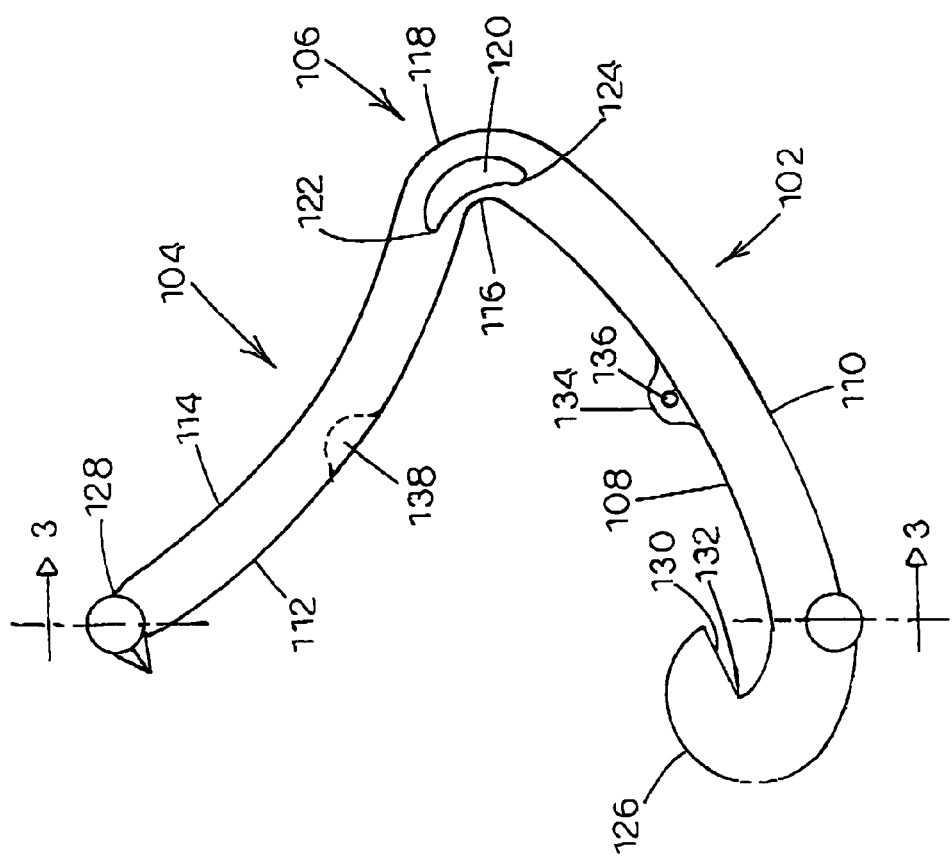
FIG. 2 is an enlarged side elevation view of the surgical clip according to one embodiment of the present invention.

Referring to FIG. 1 through FIG. 3, an example is illustrated of an asymmetric surgical clip generally designated 100 that is suitable for use in conjunction with the present invention. Clip 100 and others of similar design are particularly useful as suture clips that may secure the free ends of a suture. Clip 100 may be constructed from any suitable biocompatible material, such as certain metals and polymers. However, the present invention is particularly suitable for practice with polymeric clips. Thus, clip 100 preferably comprises a one-piece integral polymeric body formed from a suitably strong biocompatible engineering plastic, such as the type commonly used for surgical implants. Examples include polyethylene terephthalate (PET), polybutylene terephthalate (PBT), polyoxymethylene, or other thermoplastic materials having similar properties that can be injection-molded, extruded or otherwise processed into like articles.

FIG. 1 is an enlarged perspective view of the surgical clip of the present invention. The body of clip 100 includes a first or outer leg, generally designated 102, and a second or inner leg, generally designated 104. First and second legs 102 and 104 are joined at their proximal ends by an integral hinge section, generally designated 106. First and second legs 102 and 104 have complementary arcuate profiles. Thus, first leg 102 has a concave inner surface 108 and a convex outer surface 110, and second leg 104 has a convex innersurface 112 and a concave outer surface 114. Convex inner surface 112 of second leg 104 and concave inner surface 108 of first leg 102 have substantially matching radii of curvature.

Hinge section 106 has a continuous concave inner surface 116 and a continuous convex outer surface 118. Concave inner surface 116 of hinge section 106 joins concave inner surface 108 of first leg 102 and convex inner surface 112 of second leg 104. Convex outer surface 118 of hinge section 106 joins convex outer surface 110 of first leg 102 and concave outer surface 114 of second leg 104. Curved slot 120 is located between curved hinge surfaces 116 and 118, and is positioned closer to inner surface 116 than to outer surface 118. Slot 120 extends completely through hinge section 106 from side to side and its opposite ends 122, 124 extend into the proximal ends of first and second legs 102 and 104, respectively. Slot 120 provides added flexibility to hinge section 106.

First leg 102 transitions to a curved, C-shaped hook section 126 at its distal end. Second leg 104 transitions to a pointed tip section 128 at its distal end. The distal portion of hook section 126 curves inwardly and points generally toward inner surface 116 of hinge 106. The hook section 126 has a transverse beveled surface 130 and a concave inner surface 108 that define a latching recess 132. The latching recess 132 is adapted for conformally engaging tip section 128 in the course of compressing clip 100 into a latched or locked position.

In accordance with the present invention, ridge 134 protrudes from a portion of inner surface 108 of first leg 102. Ridge 134 is primarily oriented longitudinally along a portion of inner surface 108 of first leg 102. As shown in FIG. 2, which is an enlarged side elevation view of the suture clip of the present invention, the proximal and distal ends of ridge 134 may smoothly transition into the inner surface 108 of first leg 102. Eyelet 136 extends through ridge 134 in a direction substantially perpendicular to the lengthwise orientation of ridge 134 and substantially parallel to the inner surface of first leg 102. Eyelet 136 is sized large enough to permit the suture thread T to be inserted through eyelet 136, for example with the assistance of a suture needle, yet still provide sufficient resistance to facilitate secure positioning of clip 100 along the suture.

Recessed groove 138 is formed longitudinally along a portion of inner surface 112 of second leg 104. Groove 138 has a profile complementary to ridge 134 and is positioned opposite to ridge 134. Ridge 134 and groove 138 form complementary parts of an interlocking mechanism. Accordingly, when clip 100 is compressed into a latched or locked position, ridge 134 fits within groove 138. One would appreciate that groove 138 should be larger than ridge 134 to accommodate ridge 134 and the portion of the suture that passes through eyelet 136.

As best shown in FIG. 3, which is a view directed into the open concave side of clip 100 viewed along line 3—3 in FIG. 2, clip 100 has parallel, opposed side surfaces 140, 142 and 144, 146. Ridge 134 is approximately centered between side surfaces 140 and 142 of first leg 102. Similarly, groove 138 is approximately centered between side surfaces 144 and 146 of second leg 104. By centering groove 138 between side surfaces 144 and 146, approximately equal amounts of clip material are on each of the lateral sides of groove 138 and help secure the suture. The width and length of ridge 134 is smaller than the width and length of groove 138. As noted above, the larger dimensions of groove 138 can accommodate ridge 134 and the portion of the suture that passes through eyelet 136. Although ridge 134 is preferably mounted on first leg 102, an alternative embodiment contemplated by the applicants to be within the scope of the invention is to provide ridge 134 on second leg 104 and groove 138 on first leg 102 (see FIG. 2-A).

Adjacent to the distal end of the first leg 102 and immediately inward of hook section 126, cylindrical bosses 148 and 150 protrude perpendicular to each of the opposed side surfaces 140 and 142. In the illustrated example of clip 100, a bridge section 152 couples bosses 148 and 150 together. As evident in FIG. 2, bosses 148 and 150 project outwardly beyond convex outer surface 110 of first leg 102. At the distal end of second or inner leg 104, cylindrical bosses 154 and 156 protrude perpendicular to each of the opposed side surfaces of inner leg 104 at tip section 122. Bosses 154 and 156 of second leg 104 extend longitudinally forwardly beyond tip section 128.

In the practice of securing a suture as understood by persons skilled in the art, clip 100 is designed to be compressed into a latched or locked position around a suture through the use of an appropriate clip applicator instrument, such as the type described in the aforementioned U.S. Pat. No. 5,100,416 to Oh et al. The clip applicator instrument engages bosses 148, 150, 154 and 156 of clip 100 and pivots bosses 148, 150, 154 and 156 inwardly about hinge section 106. This causes first and second legs 102 and 104 to close around the vessel, with convex inner surface 112 of second leg 104 and complementary concave inner surface 108 of first leg 102 contacting the outer wall of the vessel. Ridge 134 pushes a portion of the suture into groove 138. Ridge 134 and groove 138 effectively secure the clip to the vessel and maintain a desired amount of tension on the suture after clip closure. Tip section 128 of second leg 104 then begins to contact hook section 126. Further pivotal movement by the applicator instrument longitudinally elongates first leg 102 and deflects hook section 126, allowing tip section 128 to align with latching recess 132. Upon release of the applicator instrument, tip section 128 snaps into and is conformably seated in latching recess 132, at which point clip 100 is in its latched condition. In the latched condition, tip section 128 is engaged between concave inner surface 108 and beveled surface 130.

FIG. 4 is an enlarged, fragmentary perspective view of the ridge 134 and groove 138 portions of clip 100. One would appreciate that the proximity of ridge 134 and groove 138 suggests that clip 100 is in the process of being compressed into the closed position. Both ends of suture thread T are threaded through eyelet 136 by, for example, inserting a suture needle through eyelet 136, suturing the tissue, and again inserting the suture needle through eyelet 136.

FIG. 5 is an enlarged, vertical cross-sectional view of the ridge 134 and groove 138 portions of clip 100 as viewed from the open end of clip 100, as in FIG. 3. One would appreciate that the proximity of ridge 134 and groove 138 suggests that clip 100 is in the process of being compressed into the closed position. FIG. 5 shows the lateral alignment of ridge 134 and groove 138.

FIG. 6 is an enlarged, vertical cross-sectional view of clip 100 engaged around a portion of suture thread T. In the area where clip 100 is applied to suture thread T, ridge 134 pushes suture thread T into groove 138. The portion of suture thread T in contact with ridge 134 conforms around ridge 134 as suture thread T is pushed into groove 138. The desired amount of tension is maintained on suture thread T primarily by the interaction between ridge 134, suture thread T, and the interior walls of groove 138.

Figure 7:
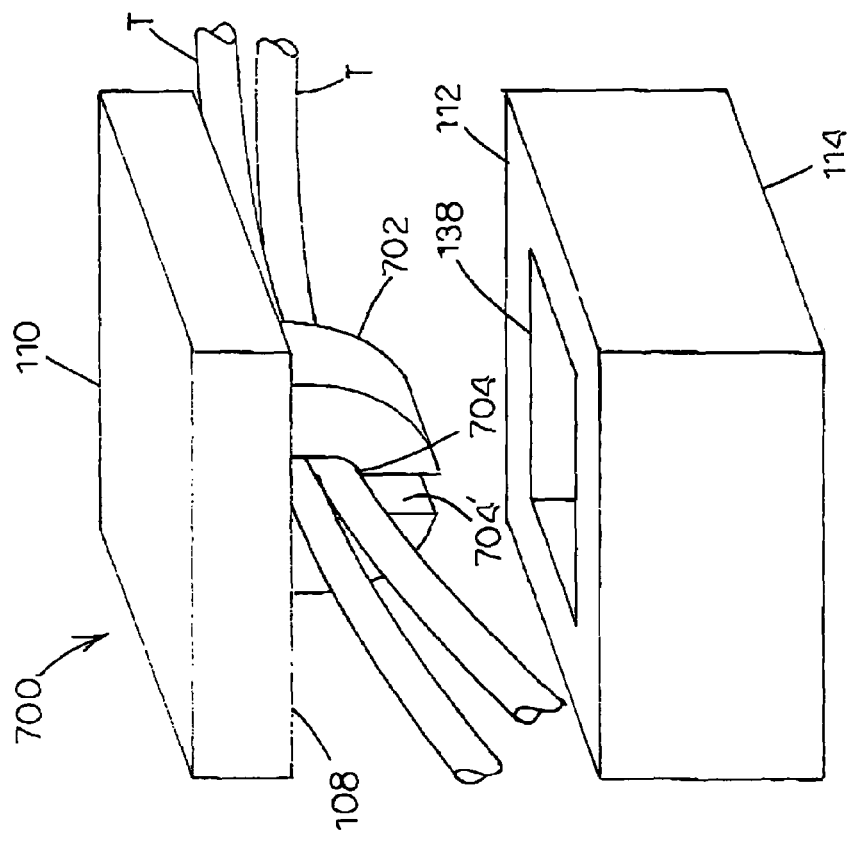
FIG. 7 is an enlarged, fragmentary perspective view of the ridge and groove portions of the surgical clip according to another embodiment of the present invention.
Figure 8:
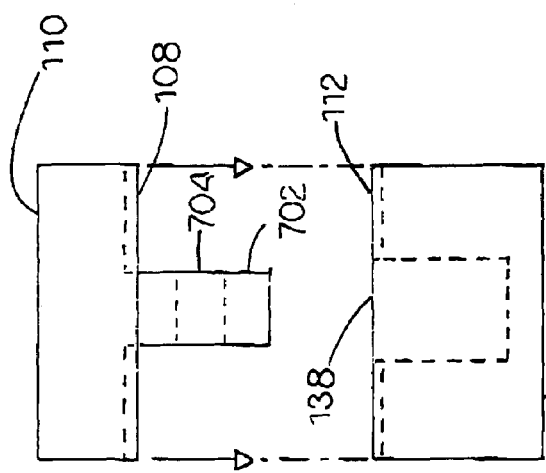
FIG. 8 is a vertical cross-sectional view of the ridge and groove portions of the surgical clip according to another embodiment of the present invention.
Figure 9:
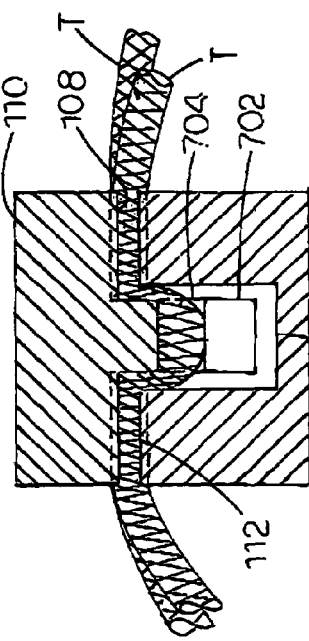
FIG. 9 is a vertical cross-sectional view of the clip applied to a suture.

FIGS. 7–9 depict a portion of an alternate embodiment of a suture clip 700 in accordance with the invention. Clip 700 is identical to clip 100 (described above with reference to FIGS. 1–6) in every respect, with the exception of ridge 702 and eyelet 704, which are shown in detail in FIGS. 7–9. In this embodiment, eyelet 704 extends transversely through ridge 702 perpendicular to the lengthwise direction of inner surface 108 of first leg 102. Ridge 702 comprises an aperture or eyelet 704 that extends downwardly through the bottom of ridge 702 so as to define an open slot 704' that extends from the bottom of ridge 702 into eyelet 704 to facilitate inserting suture thread T through eyelet 704. As a result, ridge 702 has a generally U-shaped profile, which facilitates the placement of clip 700 around suture thread T. For example, clip 700 may be applied to suture thread T after suture thread T has been used to secure tissue.

As in the previous embodiment, clip 700 secures suture thread T in a manner similar to clip 100. As shown in FIG. 9, when clip 700 is applied to a portion of suture thread T, ridge 702 pushes suture thread T into groove 138. The portion of suture thread T in contact with ridge 702 conforms around ridge 702 as suture thread T is pushed into groove 138. The desired amount of tension is maintained on suture thread T primarily by the interaction between ridge 702, suture thread T, and the interior walls of groove 138.

Accordingly, the objects of the invention have been fulfilled by providing a surgical clip that may be used to secure the ends of a suture while maintaining a desired amount of tension on the suture.

It will be understood that various details of the invention may be changed without departing from the scope of the invention. Furthermore, the foregoing description is for the purpose of illustration only, and not for the purpose of limitation—the invention being defined by the claims.

What is claimed is:

1. A polymeric surgical clip comprising:
   (a) a first leg member having an inner surface and an opposite outer surface;
   (b) a second leg member having an inner surface and an opposite outer surface;
   (c) a resilient hinge joining the first leg member and the second leg member at their proximal ends, the first and second leg members being oriented such that the inner surface of the first leg member is in opposition to the inner surface of the second leg member;
   (d) a deflectable hook member terminating the distal end of the first leg member, the hook member being curved toward the second leg member;
   (e) a locking portion terminating the distal end of the second leg member, the locking portion being complementary to the hook member such that when said first and second leg members are moved about the hinge from an open position to a closed position, the hook member deflects about the distal end of the second leg member to lock the clip in the closed position; and
   (f) a suture securing mechanism comprising:
      (i) a ridge formed along the inner surface of one of the first and second leg members, the ridge having an eyelet extending therethrough; and
      (ii) a groove formed along the inner surface of the other of the first and second leg members than the one upon which the ridge is formed, the groove being aligned in opposition to the ridge wherein the ridge and groove cooperate when the clip is in the closed position to capture a portion of a suture threaded through the eyelet and to maintain a desired level of tension on the suture.

2. The polymeric surgical clip of claim 1, wherein the ridge is oriented along a primary axis, the primary axis running generally parallel to the longitudinal axis of the first and second leg members.

3. The polymeric surgical clip of claim 2, wherein the eyelet extends through the ridge perpendicular to the primary axis and parallel to the inner surfaces of the first and second leg members.

4. The polymeric surgical clip of claim 2, wherein the eyelet extends through the ridge perpendicular to the longitudinal axis of the first and second leg members.

5. The polymeric surgical clip of claim 1, wherein the ridge is formed along the inner surface of the first leg member and the groove is formed along the inner surface of the second leg member.

6. The polymeric surgical clip of claim 1, wherein the ridge is formed along the inner surface of the second leg member and the groove is formed along the inner surface of the first leg member.

7. The polymeric surgical clip according to claim 1, wherein the inner surface of the first leg member has a concave radius of curvature between the hinge and the hook member and the outer surface of the first leg member has a convex radius of curvature, the inner surface of the second leg member has a convex radius of curvature between the hinge and its distal end and the outer surface of the second leg member has a concave radius of curvature between the hinge and its distal end.

8. The polymeric surgical clip according to claim 1, wherein the clip comprises bosses coupled to the first and second leg members for engagement with a suitable clip applier for applying the clips, the bosses joined in pairs to opposite sides of the first leg member between the hinge and the hook portion, and to opposite sides of the second leg member at the distal end of the second leg member, the second leg member having sharp pointed members extending from the bosses.

9. The polymeric surgical clip according to claim 8, wherein a portion of the pair of bosses joined to the first leg member extend beyond the outer surface of the first leg member to form substantially parallel and spaced apart surfaces which prevent lateral movement of the first and second leg members relative to one another when the clip is in the closed position.

10. A polymeric surgical clip comprising:
  (a) a first leg member having an inner surface and an opposite outer surface;
  (b) a second leg member having an inner surface and an opposite outer surface;
  (c) a resilient hinge joining the first leg member and the second leg member at their proximal ends, the first and second leg members being oriented such that the inner surface of the first leg member is in opposition to the inner surface of the second leg member;
  (d) a deflectable hook member terminating the distal end of the first leg member, the hook member being curved toward the second leg member;
  (e) a locking portion terminating the distal end of the second leg member, the locking portion being complementary to the hook member such that when said first and second leg members are moved about the hinge from an open position to a closed position, the hook member deflects about the distal end of the second leg member to lock the clip in the closed position; and
  (f) a suture securing mechanism comprising:
    (i) a ridge formed along the inner surface of one of the first and second leg members, the ridge being oriented along a primary axis, the primary axis running generally parallel to the longitudinal axis of the first and second leg members, the ridge having an eyelet extending through the ridge perpendicular to the primary axis and parallel to the inner surfaces of the first and second leg members; and
    (ii) a groove formed along the inner surface of the other of the first and second leg members than the one upon which the ridge is formed, the groove being aligned in opposition to the ridge wherein the ridge and groove cooperate when the clip is in the closed position to capture a portion of a suture threaded through the eyelet and to maintain a desired level of tension on the suture.

11. The polymeric surgical clip according to claim 10, wherein the inner surface of the first leg member has a concave radius of curvature between the hinge and the hook member and the outer surface of the first leg member has a convex radius of curvature, the inner surface of the second leg member has a convex radius of curvature between the hinge and its distal end and the outer surface of the second leg member has a concave radius of curvature between the hinge and its distal end.

12. The polymeric surgical clip according to claim 10, wherein the clip comprises bosses coupled to the first and second leg members for engagement with a suitable clip applier for applying the clips, the bosses joined in pairs to opposite sides of the first leg member between the hinge and the hook portion, and to opposite sides of the second leg member at the distal end of the second leg member, the second leg member having sharp pointed members extending from the bosses.

13. The polymeric surgical clip according to claim 12, wherein a portion of the pair of bosses joined to the first leg member extend beyond the outer surface of the first leg member to form substantially parallel and spaced apart surfaces which prevent lateral movement of the first and second leg members relative to one another when the clip is in the closed position.

14. A polymeric surgical clip comprising:
  (a) a first leg member having an inner surface and an opposite outer surface;
  (b) a second leg member having an inner surface and an opposite outer surface;
  (c) a resilient hinge joining the first leg member and the second leg member at their proximal ends, the first and second leg members being oriented such that the inner surface of the first leg member is in opposition to the inner surface of the second leg member;
  (d) a deflectable hook member terminating the distal end of the first leg member, the hook member being curved toward the second leg member;
  (e) a locking portion terminating the distal end of the second leg member, the locking portion being complementary to the hook member such that when said first and second leg members are moved about the hinge from an open position to a closed position, the hook member deflects about the distal end of the second leg member to lock the clip in the closed position; and
  (f) a suture securing mechanism comprising:
    (i) a ridge formed along the inner surface of one of the first and second leg members, the ridge being oriented along a primary axis, the primary axis running generally parallel to the longitudinal axis of the first and second leg members, the ridge having an eyelet extending through the ridge perpendicular to the longitudinal axis of the first and second leg members; and
    (ii) a groove formed along the inner surface of the other of the first and second leg members than the one upon which the ridge is formed, the groove being aligned in opposition to the ridge wherein the ridge and groove cooperate when the clip is in the closed position to capture a portion of a suture threaded through the eyelet and to maintain a desired level of tension on the suture.

15. The polymeric surgical clip according to claim 14, wherein the inner surface of the first leg member has a concave radius of curvature between the hinge and the hook member and the outer surface of the first leg member has a convex radius of curvature, the inner surface of the second leg member has a convex radius of curvature between the hinge and its distal end and the outer surface of the second leg member has a concave radius of curvature between the hinge and its distal end.

16. The polymeric surgical clip according to claim 14, wherein the clip comprises bosses coupled to the first and second leg members for engagement with a suitable clip applier for applying the clips, the bosses joined in pairs to opposite sides of the first leg member between the hinge and the hook portion, and to opposite sides of the second leg member at the distal end of the second leg member, the second leg member having sharp pointed members extending from the bosses.

17. The polymeric surgical clip according to claim 16, wherein a portion of the pair of bosses joined to the first leg member extend beyond the outer surface of the first leg member to form substantially parallel and spaced apart surfaces which prevent lateral movement of the first and second leg members relative to one another when the clip is in the closed position.

\* \* \* \* \*